United States Patent [19]

Trumbo

[11] Patent Number: 5,889,098
[45] Date of Patent: Mar. 30, 1999

[54] LATEX FORMULATIONS CONTAINING ETHYLENICALLY-UNSATURATED 1,3 DIKETOAMIDE FUNCTIONAL POLYMERS

[75] Inventor: David L. Trumbo, Racine, Wis.

[73] Assignee: S. C. Johnson Commercial Markets, Inc., Sturtevant, Wis.

[21] Appl. No.: 864,474

[22] Filed: May 28, 1997

Related U.S. Application Data

[62] Division of Ser. No. 518,941, Aug. 24, 1995.

[51] Int. Cl.$^6$ ..................................................... C08L 37/00
[52] U.S. Cl. ........................................... 524/241; 524/555
[58] Field of Search ................................... 524/543, 241, 524/555

[56] References Cited

U.S. PATENT DOCUMENTS

| | | | |
|---|---|---|---|
| 3,459,790 | 8/1969 | Smith | 260/483 |
| 3,488,708 | 1/1970 | Smith | 96/84 |
| 3,939,130 | 2/1976 | Ponticello | 260/65 |
| 4,215,195 | 7/1980 | Ponticello et al. | 430/496 |
| 4,247,673 | 1/1981 | Ponticello et al. | 526/263 |
| 4,275,229 | 6/1981 | Mylonakis et al. | 562/459 |
| 4,346,231 | 8/1982 | Ponticello et al. | 560/178 |
| 4,408,018 | 10/1983 | Bartman et al. | 525/300 |
| 4,421,915 | 12/1983 | Ponticello et al. | 544/387 |
| 4,429,096 | 1/1984 | Schaefer | 526/287 |
| 4,438,278 | 3/1984 | Ponticello et al. | 560/205 |
| 4,687,809 | 8/1987 | Kamikeseda et al. | 525/57 |
| 4,772,680 | 9/1988 | Noomen et al. | 528/229 |
| 4,855,349 | 8/1989 | Ingle | 524/432 |
| 4,906,684 | 3/1990 | Say | 524/548 |
| 4,910,249 | 3/1990 | Kania et al. | 524/555 |
| 4,929,661 | 5/1990 | Noomen et al. | 524/259 |
| 4,987,177 | 1/1991 | Den Hartog et al. | 524/517 |
| 4,987,186 | 1/1991 | Akiyama et al. | 525/107 |
| 5,055,510 | 10/1991 | Kissel | 524/211 |
| 5,070,136 | 12/1991 | Dersch et al. | 524/555 |
| 5,098,974 | 3/1992 | Kania et al. | 526/310 |
| 5,157,071 | 10/1992 | Ingle | 524/516 |
| 5,221,581 | 6/1993 | Palmer et al. | 428/425.8 |
| 5,498,659 | 3/1996 | Esser | 524/549 |

FOREIGN PATENT DOCUMENTS

| | | |
|---|---|---|
| 136 411 A1 | 4/1985 | European Pat. Off. . |
| 262 720 A1 | 4/1988 | European Pat. Off. . |
| 390 370 A1 | 10/1990 | European Pat. Off. . |
| 417 824 A1 | 3/1991 | European Pat. Off. . |
| 438 216 A2 | 7/1991 | European Pat. Off. . |
| 492 847 A2 | 7/1992 | European Pat. Off. . |
| 102 308 | 12/1973 | German Dem. Rep. . |
| 2535372 A1 | 2/1977 | Germany . |
| 93/16133 | 8/1993 | WIPO . |
| 94/09045 | 4/1994 | WIPO . |

OTHER PUBLICATIONS

J.S. Witzeman et al., "Transacetoacetylation with tert–Butyl Acetoacetate: Synthetic Applications" *The Journal of Organic Chemistry*, vol. 56(5), pp. 1713–1718 (1991).

F. Del Rector et al.,"Synthesis of Acetoacetylated Resins and Applications for Acetoacetate Chemistry in Thermoset Coatings," *Polymers Paint Colour Journal*, vol. 180, No.4264, pp. 462–470 (Jul. 4, 1990).

F. Del Rector et al., "Applications for the Acetoacetyl Functionality in Thermoset Coatings," Paper given at Water––Borne and Higher Solids Coatings Symposium, Feb. 3–5, 1988, New Orleans, LA, 26 pages.

R.W. Carling et al., "3–Nitro–3, 4–dihydro–2(1H)–quinolones," *Journal of Medicinal Chemistry*, vol. 36, No. 22, 1993, pp. 3397–3408.

*Primary Examiner*—Jeffery T. Smith
*Assistant Examiner*—W. C. Cheng
*Attorney, Agent, or Firm*—Renee J. Rymarz

[57] ABSTRACT

A novel ethylenically-unsaturated 1,3-diketoamide functional compound, polymers comprised thereof, and latex formulations containing polymeric ingredients having 1,3-diketoamide functional pendant moieties are disclosed. The 1,3-diketoamide functional pendant moieties have excellent hydrolytic stability.

17 Claims, No Drawings

LATEX FORMULATIONS CONTAINING ETHYLENICALLY-UNSATURATED 1,3 DIKETOAMIDE FUNCTIONAL POLYMERS

This is a divisional of application Ser. No. 08/518,941 pending filed Aug. 24, 1995.

BACKGROUND OF THE INVENTION

1. Field of the Invention

This invention is related to ethylenically-unsaturated 1,3-diketoamide functional compounds and polymers prepared therefrom. The invention is also related to latex formulations containing polymeric ingredients having 1,3-diketoamide functional pendant moieties which advantageously exhibit excellent hydrolytic stability.

2. Related Background Art

Ethylenically-unsaturated monomers containing active methylene groups such as $$-\overset{O}{\underset{\|}{C}}-CH_2-\overset{O}{\underset{\|}{C}}-$$

and polymers prepared from such monomers having pendant active methylene groups have long been known. For example, U.S. Pat. No. 3,459,790 discloses acetoacetates, such as 2-acetoacetoxyethyl methacrylate and 2-acetoacetoxyethyl acrylate, for forming polymers to be used as gelatin extenders or substitutes in photographic films.

Polymerizable compounds having amide groups and active methylene crosslinking sites in side chains extending from ethylenically unsaturated backbones are disclosed in U.S. Pat. No. 4,215,195. These polymerizable compounds, which are used to form polymers which can act as polymeric color couplers, binders and gelatin extenders, are generically represented by the formula:

$$CH_2=\overset{R}{\underset{|}{C}}-\overset{O}{\underset{\|}{C}}-Z-\overset{O}{\underset{\|}{C}}-CH_2-R^1$$

wherein R is hydrogen or methyl; $R^1$ is cyano or

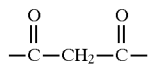

wherein $R^2$ is alkyl; Z is $-X-R^3-X-$ or

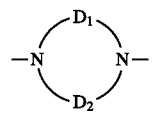

wherein each $-X-$ is $-O-$ or $-NR^4-$, provided at least one $-X-$ is $-NR^4-$, wherein $R^4$ is hydrogen or alkyl, $R^3$ is divalent hydrocarbon and $D_1$ and $D_2$ together are carbon atoms necessary to complete a 5 to 7 membered ring. Acetoacetamidoethyl methacrylate is exemplified as a useful polymerizable monomer.

The preparation of various acetoacetates and acetoacetamides is well known For example, J. Witzeman, et al., The Journal of Organic Chemistry, 56, 1713–18 (1991) discloses the preparation of acetoacetates and acetoacetamides by reaction of various nucleophiles with tert-butyl acetoacetates. This reference reports that acetoacetylated materials may be used as chemical intermediates in the pharmaceutical, agrichemical, chemical and polymer industries.

More particularly, it is known to use acetoacetoxy-functional moiety-containing polymers in combination with polyfunctional amines in latex compositions. Such compositions may be applied to substrates to form films by crosslinking the amines with the acetoacetoxy-functional moiety through the formation of enamine linkages. For example, PCT International Publication No. WO 93/16133 discloses a particularly advantageous storage-stable single-package latex formulation containing a polymeric ingredient having at least acetoacetoxy functional pendant moieties. This reference discloses that preferred acetoacetoxy functional moiety-containing ingredients include acetoacetamides, such as acetoacetamide methacrylate and acetoacetamide acrylate, as well as acetoacetoxyethyl methacrylate ("AAEM"), acetoacetoxyethyl acrylate ("AAEA"), allyl acetoacetate and vinyl acetoacetate. The use of acetoacetamides in a latex formulation is not exemplified. None of these references disclose or suggest an acetoacetamide compound having an arylene radical therein, or the use of such an acetoacetamide in a latex formulation.

U.S. Pat. No. 5,098,974 discloses an acrylic polymer, which is used as a pigment grinding vehicle having pendent tertiary alkyl primary amine groups and at least one other pendent functionality reactive with isocyanate groups. The monomer having pendent tertiary alkyl primary amine groups may be prepared by reacting a tertiary alkyl isocyanate, such as meta-isopropenyl-α, α-dimethylbenzyl isocyanate, with a tertiary alcohol, such as diacetone alcohol (4-hydroxy-4-methyl-2-pentanone), in the presence of a catalyst. There is no disclosure or suggestion, however, of preparing acetoacetamides.

While the acetoacetoxy functional moiety-containing ingredients disclosed in WO 93/16133 may be used to provide desirable latex formulations, there is a continuing need for improved hydrolytic stability of acetoacetoxy functional moieties employed in aqueous polymer formulations. A latex formulation having acetoacetoxy functional pendent moieties with improved hydrolytic stability will advantageously have enhanced storage stability and thus significant commercial advantage over prior art formulations.

SUMMARY OF THE INVENTION

This invention relates to novel ethylenically-unsaturated 1,3-diketoamide functional compounds represented by the formula (I):

$$A-\overset{O}{\underset{\|}{C}}-\overset{R^5}{\underset{|}{CH}}-\overset{O}{\underset{\|}{C}}-B \qquad (I)$$

wherein $R^5$ is hydrogen, alkyl having 1 to 10 carbon atoms, aryl having 6 to 20 carbon atoms or aralkyl having 7 to 20 carbon atoms;

A is a group represented by the formula

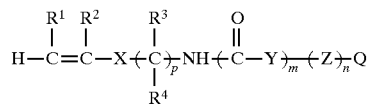

wherein $R^1$ is hydrogen, alkyl having 1 to 10 carbon atoms, aryl having 6 to 20 carbon atoms or aralkyl having 7 to 20 carbon atoms;

$R^2$ is hydrogen, alkyl having 1 to 10 carbon atoms, aryl having 6 to 20 carbon atoms or aralkyl having 7 to 20 carbon atoms;

X is arylene having 6 to 20 carbon atoms;

R$^3$ and R$^4$ are independently hydrogen, alkyl having 1 to 10 carbon atoms, aryl having 6 to 20 carbon atoms or aralkyl having 7 to 20 carbon atoms;

Y is —NH— or —O—;

Z is alkylene having 1 to 10 carbon atoms;

m, n and p are independently 0 or 1; and

Q is O or a single bond; and

B is A, an alkyl group having 1 to 10 carbon atoms, aryl having 6 to 20 carbon atoms or aralkyl having 7 to 20 carbon atoms. Exemplary arylene radicals include, without limitation, phenylene, naphthylene or the like, which can be substituted or unsubstituted. Preferably X is phenylene and p is 1.

The invention is also directed to a polymer derived from at least the ethylenically-unsaturated 1,3-diketoamide functional compound of formula I. The polymer may be a homopolymer or a copolymer of the ethylenically-unsaturated 1,3-diketoamide functional compound and an addition-copolymerizable monomer. Such addition-copolymerizable monomers are well known to those of ordinary skill in the art and include, for example, ethylenically-unsaturated compounds and the like. A preferred embodiment of the invention relates to a polymer comprising both acid functional pendant moieties derived from ethylenically-unsaturated acid functional compounds and ethylenically-unsaturated 1,3-diketoamide functional pendant moieties derived from the 1,3-diketoamide functional compound of formula I.

Yet another embodiment of this invention is directed to a latex formulation containing (a) a polymeric ingredient having at least 1,3-diketoamide functional pendant moieties derived from the 1,3-diketoamide functional compound of formula I, (b) a polyfunctional amine and (c) an evaporable aqueous carrier. Preferably, the polyfunctional amine is a non-polymeric polyfunctional amine. The latex formulation can take the form of a single-package latex formulation, i.e., a formulation which is stored or shipped with the polymeric ingredient combined with the polyfunctional amine, or a two-package latex formulation where the polymeric ingredient and the amine remain separate until shortly prior to use. If an alkali soluble formulation is desired, the latex formulations of the invention preferably also contain acid functional pendant moieties within the same polymeric ingredient having the 1,3-diketoamide functional pendant moieties or in a separate polymeric ingredient. In a single-package latex formulation having carboxyl functionality it is also preferred to include an effective amount of volatile base in the latex formulation to inhibit crosslinking of the 1,3-diketoamide functional pendant moieties and the polyfunctional amine. The 1,3-diketoamide functional moiety employed in the polymers and latex formulations of this invention advantageously exhibits excellent hydrolytic stability so that such formulations can be stored for long periods of time without degradation of the 1,3-diketoamide functionality.

DETAILED DESCRIPTION OF THE INVENTION

The ethylenically-unsaturated 1,3-diketoamide functional compounds of this invention are represented by previously described formula I. The preferred ethylenically-unsaturated 1,3-diketoamide functional compounds of this invention are represented by the formula (II):

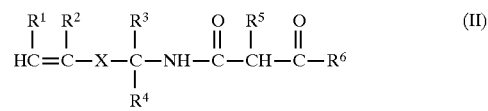

wherein R$^1$ is hydrogen, alkyl having 1 to 10 carbon atoms, aryl having 6 to 20 carbon atoms, aralkyl having 7 to 20 carbon atoms, halo, —CO$_2$CH$_3$ or —CN;

R$^2$ is hydrogen, alkyl having 1 to 10 carbon atoms, aryl having 6 to 20 carbon atoms or aralkyl having 7 to 20 carbon atoms;

X is arylene having 6 to 20 carbon atoms;

R$^3$, R$^4$ and R$^5$ are independently hydrogen, alkyl having 1 to 10 carbon atoms, aryl having 6 to 20 carbon atoms or aralkyl having 7 to 20 carbon atoms; and R$^6$ is alkyl having 1 to 10 carbon atoms, aryl having 6 to 20 carbon atoms or aralkyl having 7 to 20 carbon atoms. Preferably X is phenylene. It is also preferred that R$^1$ and R$^5$ are hydrogen, while R$^3$, R$^4$ and R$^6$ are methyl groups. More preferably, R$^2$ is hydrogen or a methyl group.

Exemplary ethylenically-unsaturated 1,3-diketoamide functional compounds of this invention include, without limitation, 3-isopropenyl-α,α-dimethylbenzyl amidoacetoacetate, 4-isopropenyl-α,α-dimethylbenzyl amidoacetoacetate, 4-ethylenyl-phenyl amidoacetoacetate and the like. 3-isopropenyl-α,α-dimethylbenzyl amidoacetoacetate and 4-isopropenyl-α,α-dimethylbenzyl amidoacetoacetate are most preferred.

The ethylenically-unsaturated 1,3-diketoamide functional compounds of this invention may be prepared using methods well known to those skilled in the art. Exemplary reaction schemes I, II and III illustrate methods for preparing the compounds of this invention. The starting materials employed in Schemes I, II and III are readily available or can be prepared by known methods, such as disclosed in U.S. Pat. No. 5,098,974, the disclosure of which is incorporated by reference herein.

Scheme I set forth below illustrates the preparation of the compounds of this invention by first reacting a aryl compound having both ethylenically-unsaturated and isocyanate substitution (e.g., meta-isopropenyl-α,α-dimethylbenzyl isocyanate ("m-TMI")) with an acetoacetate (e.g., ethyl acetoacetate) in the presents of a catalyst (e.g., dibutyltin dilaurate), to form a urethane. The urethane is then decomposed to the compound of this invention through the application of heat to the urethane in an acidic aqueous environment.

Scheme I:
(Preparation of 3-isopropenyl-α,α-dimethyl-benzyl amidoacetoacetate)

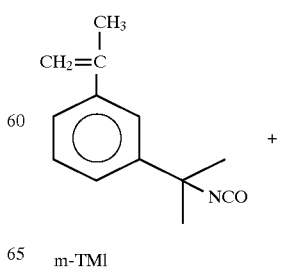

m-TMI

-continued
Scheme I:
(Preparation of 3-isopropenyl-α,α-dimethyl-
benzyl amidoacetoacetate)

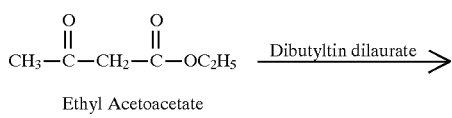

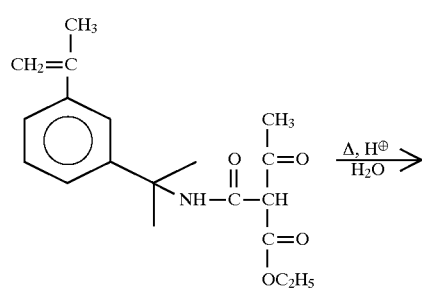

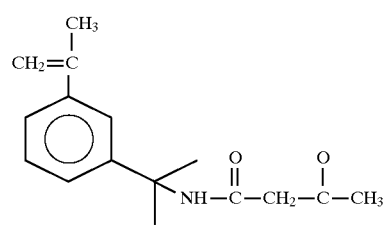

+ CO₂ & C₂H₅OH

An alternative method for preparing the compounds of this invention is illustrated in Scheme II. In this scheme an aryl compound having both ethylenically-unsaturated and isocyanate substitution (e.g., m-TMI is reacted with a tertiary alcohol (e.g., 4-hydroxy-4-methyl-2-pentanone) to form a urethane. The urethane is then decomposed by the application of heat to eliminate carbon dioxide and form the amine (e.g., 3-isopropenyl-α,α-dimethylbenzyl a mine. The amine is then contacted with an acetoacetate (e.g., t-butyl acetoacetate) with the application of heat which is believed to form a diketene-acetone adduct that reacts with the amine to form the compounds of this invention.

Scheme II:
(Alternative Method of Preparing 3-
isopropenyl-α,α-dimethyl benzyl
amidoacetoacetate)

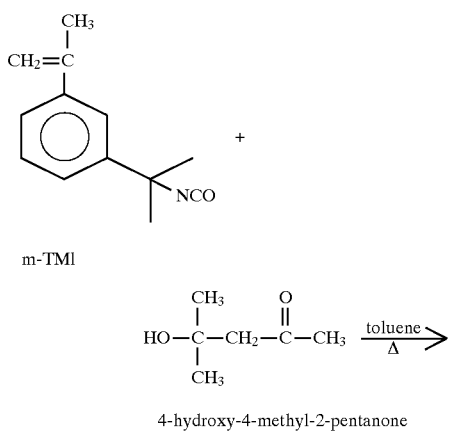

-continued
Scheme II:
(Alternative Method of Preparing 3-
isopropenyl-α,α-dimethyl benzyl
amidoacetoacetate)

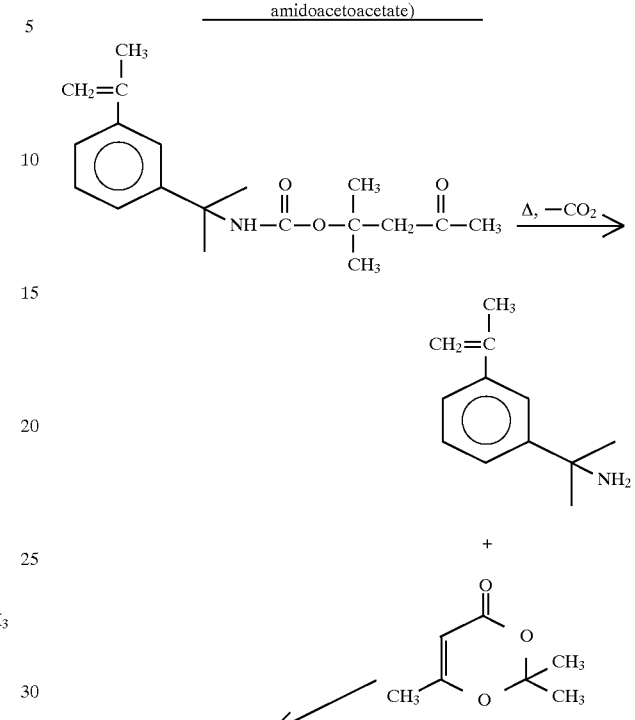

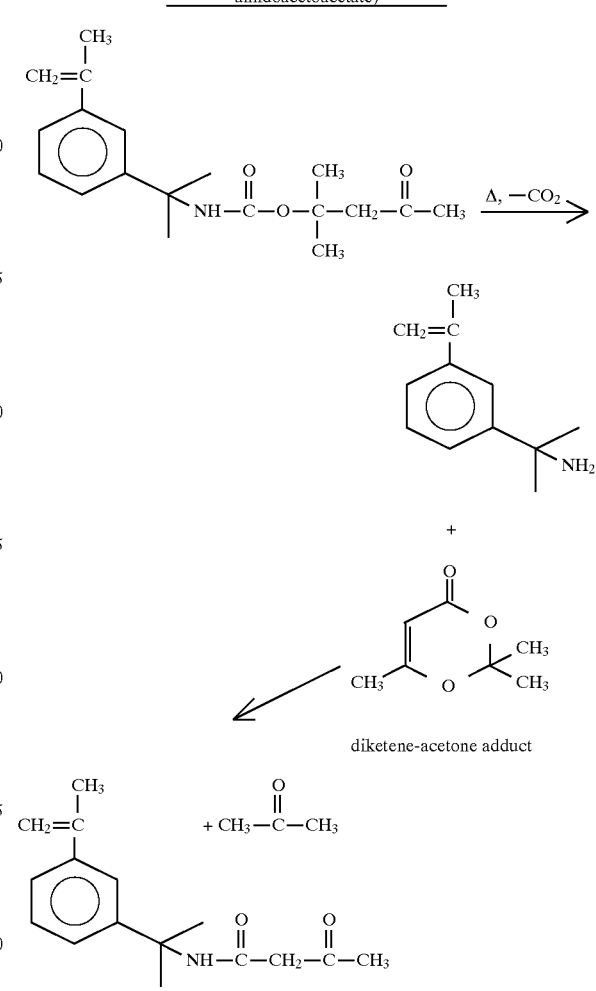

Scheme III set forth below illustrates the preparation of 4-ethylenyl-phenyl amidoacetoacetate using p-aminostyrene and a diketone-acetone adduct derived from an acetoacetate in a manner similar to that set forth in Scheme II.

Scheme III:
(Preparation of 4-ethylenyl-phenyl
amidoacetoacetate using the diketione-
acetone adduct)

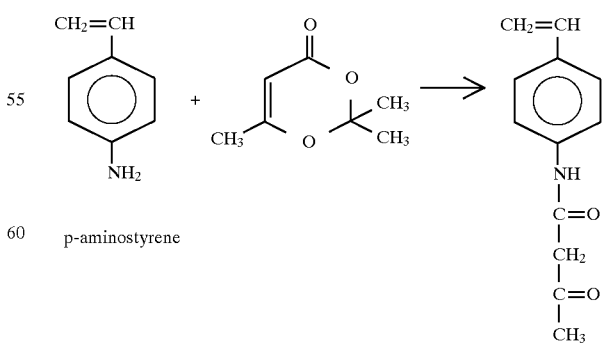

p-aminostyrene

The ethylenically-unsaturated 1,3-diketoamide functional compounds of this invention can be used to form polymers by polymerization of the ethylenically-unsaturated compounds to form a polymer backbone having 1,3-diketoamide functional pendant moieties. It is also possible to form polymers by copolymerizing the ethylenically-unsaturated 1,3-diketoamide functional compounds with other ethylenically-unsaturated copolymers. Preferably such ethylenically-unsaturated copolymers have pendant carboxylic acid functionality. In such a case the polymer possesses both 1,3-diketoamide functional pendant moieties and carboxylic acid functional pendant moieties.

Ethylenically-unsaturated carboxylic acid moiety-containing monomers suitable for purposes of the invention include but are not limited to acrylic acid, ethacrylic acid, fumaric acid-monoethyl ester, fumaric acid, itaconic acid, maleic acid, maleic anhydride, methacrylic acid, fumaric acid-monomethyl ester, methyl hydrogen maleate, and combinations thereof. However, polymers of this invention may be prepared with any addition-copolymerizable monomer that does not inhibit the 1,3-diketoamide functionality of the resulting copolymer.

Preferred ethylenically-unsaturated carboxylic acid moiety-containing monomers are selected from the group consisting of acrylic acid, methacrylic acid, and combinations thereof.

The ethylenically-unsaturated carboxylic acid moiety-containing monomers and ethylenically-unsaturated 1,3-diketoamide functional compounds can be used to make a polymer having both acid-functional pendant moieties and 1,3-diketoamide functional pendant moieties. It is also possible to prepare two separate polymers, one of which has acid-functional pendant moieties and the other having 1,3-diketoamide functional pendant moieties and mix those polymers together.

The compounds of this invention and the comonomers, if present, are typically polymerized in the presence of a catalytic amount of a conventional free-radical initiator. Suitable initiators, also called catalysts, include but are not limited to certain water-soluble initiators, various azo compounds, select redox combinations and organic peroxides. However, any initiator capable of generating free-radicals may be employed.

Suitable water-soluble initiators include but are not limited to peracetic acid; certain perborates; certain percarbonates; certain perphosphates; certain persulfates, such as sodium, potassium, ammonium, and barium persulfate; acetyl peroxide; hydrogen peroxide; hydroperoxides such as tertiary-butyl hydroperoxide; and combinations thereof. A presently preferred water-soluble free-radical initiator is ammonium persulfate.

Suitable azo initiators include but are not limited to azodiisobutyl nitrile; azobisdimethyl valeronitrile; azodiisobutyl amide; azobis(alpha-ethylbutyl nitrile); azobis(alpha, gamma-dimethyl-capronitrile); and combinations thereof.

One redox combination, suitable for purposes of the present invention, may consist of a water-soluble persulfate as the oxidizing component of the redox combination, and a hydrosulfite, e.g. sodium hydrosulfite, as the reducing component of the redox combination. It is also possible to use water-soluble bisulfites, metabisulfites and/or thiosulfates, and formaldehyde sulfoxylates in lieu of the hydrosulfites.

Industrial Applicability

The ethylenically-unsaturated 1,3-diketoamide functional compounds of this invention can be used to prepare polymers having 1,3-diketoamide functional pendant moieties. These polymers can be combined with crosslinking agents, such as polyfunctional amines, to form curable compositions or formulations. As noted previously, a preferred aspect of this invention is directed to a latex formulation containing (a) a polymeric ingredient having at least 1,3-diketoamide functional pendant moieties derived from the compound of formula I, (b) a non-polymeric polyfunctional amine and (c) an evaporable aqueous carrier. The latex formulations of this invention may be used to provide durable polymeric films and coatings for substrates, such as cardboard, paper, wood, linoleum, concrete, stone, marble and terrazzo, and a variety of metal surfaces by application thereto.

The novel latex formulations of this invention can be utilized to produce surface coatings as floor polishes, paints, adhesives and so forth. More particularly, these compositions produce durable, abrasion-resistant and solvent-resistant surface coatings or finishes on various substrates such as cardboard, concrete, counter tops, floors, marble and terrazzo, paper, stone, tile, wood and a variety of metal surfaces including polished metal surfaces and metal foils.

Still another application for the latex formulation of this invention is in the production of water-based adhesives for various consumer and industrial uses.

Industrial end-use applications include surface coatings and finishes for construct-ion machinery and equipment, for bridges and road surfaces, for various parts or components of certain production-line machinery, and for a wide assortment of automotive components.

Consumer end-use applications include durable polymeric films and surface coatings for various components of such a wide assortment of home-use appliances as clothes washers and dryers, dishwashers, radios, ranges and ovens, refrigerators, television sets, and video cassette recorders.

End-use applications for wood for industrial use, home use, and otherwise, include but are not limited to interior and exterior wood surface coatings such as stains and varnishes.

The novel latex formulations of this invention can also be used by industry or consumers as thickeners for paints and other surface coatings, as well as thickeners for printing inks and other formulations which need to crosslink upon drying. Further in that regard, various specific latex formulations produced in accordance with the principles of the present invention are able to provide certain finishes as well as other surface treatments for a number of relatively thin substrates such as paper, wherein such finishes and surface treatments are able to crosslink without liberating formaldehyde. Such an end use is particularly desirable, for example, in the production of release coatings, overprint varnishes, and especially in relation to the production of rotogravure coatings.

Yet another specific end use for the latex formulations of the present invention is in the production of a wide assortment of architectural surface coatings which need to form films of various thicknesses, at relatively low temperatures, from about 25° C. to about 0° C. and yet which provide desirable surface hardness and durability qualities, due to their crosslinked polymeric structure.

The novel latex formulation of this invention can, moreover, be shipped in bulk-sized quantities or in various smaller-sized containers, as desired. For example, to satisfy certain industrial users, the formulation of this invention can readily be shipped in 55-gallon drums, or in larger quantities such as in rail cars, if desired. Yet, if consumers desire smaller, more conveniently-sized volumetric quantities, the latex formulation can be sold in 1-gallon or smaller containers or even in conventional aerosol containers.

The latex formulations of this invention are susceptible to embodiment in various forms. Described below are several presently preferred embodiments, with the understanding that these embodiments are merely examples of the present invention and are not limiting thereof.

The term "dispersion" as used herein means a two-phase system of which one phase consists of finely-divided particles, often in the colloidal-size range, distributed throughout a bulk substance, wherein such finely-divided particles provide the disperse or internal phase and the bulk substance provides the continuous or external phase.

The term "elevated temperature" as used herein means any temperature greater than room temperature, which is 20° to 250° C.

One particular noteworthy aspect of the latex formulation of this invention, is the fact that it can be a composition having excellent hydrolytic stability and thus storage stability. The latex formulation of this invention can be a low-VOC, ("Volatile Organic Content") water-based composition of matter that may contain only one polymeric ingredient or that may contain at least two polymeric ingredients. In the former case, the polymeric ingredient must possess at least 1,3-diketoamide functional moieties and preferably possesses both acid-functional as well as 1,3-diketoamide functional pendant moieties; and in the latter case, one polymeric ingredient has acid-functional pendant moieties and the other polymeric ingredient has 1,3-diketoamide functional moieties.

If the polymeric ingredient contains both acid functionality and 1,3-diketoamide functionality, then preferably the amount of acid functionality is sufficient to provide the polymeric ingredient with an acid number in the range of about 30 to about 300; and the weight-average molecular weight ("Mw") value of such a polymeric ingredient is typically between about 2,000 and 50,000. Preferably, such a polymeric ingredient has an acid number in the range of about 50 to about 150 and a Mw value of about 2,000 to about 40,000, and more preferably a Mw value of about 2,000 to about 30,000.

However, in the case where there are at least two different polymeric ingredients, the polymeric ingredient having 1,3-diketoamide functional pendant moieties typically has an Mw value of about 2,000 to about 1,000,000. Preferably, the Mw value is between about 5,000 and about 500,000; more preferably, the Mw value is between about 15,000 and about 300,000; and most preferably, the Mw value is between about 50,000 and about 200,000. In this case the polymeric ingredient possessing acid functionality may only be polymeric in structure. Such a polymeric ingredient also preferably has an acid number in the range of about 50 to about 150 as well an Mw value of preferably about 2,000 to about 40,000, more preferably about 2,000 to about 30,000.

The latex formulation of this invention includes a polyfunctional amine containing compound. The latex formulation may be delivered either as a single-package composition or a two-package composition. In the two-package composition the polymeric ingredient is mixed with the polyfunctional amine shortly before use. In a single-package composition the polymeric ingredient and polyfunctional amine containing compound are mixed together and stored in this mixed form until use.

The preferred polyfunctional amine-containing compound, possessing at least two amine-functional moieties, is a non-polymeric polyfunctional amine-containing compound which typically has a chemical formula weight of less than about 2,000 grams per mole, and preferably has a chemical formula weight of less than about 1,000 grams per mole. However, any polyfunctional amine-containing compound that can crosslink with the 1,3-diketoamide functional pendant moieties of the polymeric ingredient may be employed in the latex formulation of this invention.

The latex formulation of this invention may be produced by combining preselected relative amounts of initiator, surfactant and evaporable aqueous carrier in an agitated reactor of suitable size, and heating the agitated reactor contents to a desired reaction temperature, typically 40° to 90° C., more preferably 75° to 85° C., over a predetermined period of time, which may typically be about 1 hour. At least one optional chain-transfer agent may also be incorporated into the agitated reactor contents at this time, if desired. Nitrogen or another suitable inert gas may be introduced into the reactor headspace to eliminate oxygen from the reaction vessel, if desired.

The surfactant ingredient or ingredients typically comprises at least one non-ionic emulsifier, at least one anionic emulsifier, or a mixture of non-ionic and anionic emulsifiers. Cationic emulsifiers as well as amphoteric emulsifiers may also be used in certain situations if desired.

Examples of useful anionic surfactants include but are not limited to organosulfates and sulfonates, for example, sodium and potassium alkyl, aryl and alkaryl sulfates and sulfonates, such as sodium 2-ethyl hexyl sulfate, potassium 2-ethyl hexyl sulfate, sodium nonyl sulfate, sodium lauryl sulfate ("NaLS"), potassium methylbenzene sulfonate, potassium toluene sulfonate, and sodium xylene sulfonate; higher fatty alcohols, for example, stearyl alcohols, lauryl alcohols, and so forth, which have been ethoxylated and sulfonated; dialkyl esters of alkali metal sulfosuccinic acid salts, such as sodium or potassium diamyl sulfosuccinates, in particular sodium dioctyl sulfosuccinate; various formaldehyde-naphthalene sulfonic acid condensation products; alkali metal salts, as well as partial alkali metal salts, and free acids of complex organic phosphate esters; and combinations thereof.

Examples of non-ionic surfactants which can be used to prepare the latex formulation of this invention include but are not limited to polyesters, for example, ethylene oxide and propylene oxide condensates which include straight and/or branched chain alkyl and alkaryl polyethylene glycol and polypropylene glycol ethers and thioethers; alkyl-phenoxy poly(ethyleneoxy) ethanols having alkyl groups containing from about 7 to about 18 carbon atoms and having from about 4 to about 240 ethyleneoxy units, such as heptyl-phenoxy poly(ethyleneoxy) ethanols, nonyl-phenoxy poly(ethyleneoxy)ethanols, and so forth; the polyoxyalkylene derivatives of hexitol, including sorbitans, sorbides, mannitans, and mannides; partial long chain fatty-acid esters, such as the polyoxyalkylene derivatives of sorbitan monolaurate, sorbitan monopalmitate, sorbitan monostearate, sorbitan tristearate, sorbitan monooleate, and sorbitan trioleate; the condensates of ethylene oxide with a hydrophobic base, such as a base that is formed by condensing propylene oxide with propylene glycol; sulfur-containing condensates, for example, those prepared by condensing ethylene oxide with higher alkyl mercaptans, such as nonyl, dodecyl, or tetradecyl mercaptan, or with alkyl thiophenols wherein the alkyl group contains from about 6 to about 15 carbon atoms; ethylene oxide derivatives of long-chain carboxylic acid, such as lauric, myristic, palmitic, or oleic acids or mixtures of acids, such as tall oil fatty acids; ethylene oxide derivatives of long chain alcohols such as octyl, decyl, lauryl, or cetyl alcohols; and combinations thereof.

In the preparation of certain preferred embodiments of the latex formulations of the invention, the evaporable carrier will consist essentially of water only. However, in the preparation of certain other embodiments of the latex formulations of the invention, it will be desirable that the evaporable carrier comprise water and at least one other water-miscible volatile organic liquid, wherein the amount of VOC does not exceed 200 grams per liter of the formulation.

Examples of water-miscible volatile organic liquids that are useful in this regard include but are not limited to alcohols; dialkyl ethers; ethylene and propylene glycols and their monoalkyl and dialkyl ethers; relatively low formula weight polyethylene oxides and their alkyl and dialkyl ethers (i.e., having a chemical-formula weight of less than about 200 grams per mole); dimethyl formamide; dimethyl acetamide; and combinations thereof.

After the desired reaction temperature is achieved, an emulsion-polymerizable mixture is incorporated into the agitated reactor contents over a predetermined period of time, such as 1 hour, while maintaining the desired reaction temperature.

The emulsion-polymerizable mixture includes at least one 1,3-diketoamide functional moiety-containing monomeric ingredient. Preferably, the mixture will also contain at least one acid moiety-containing monomeric ingredient, which is typically ethylenically-unsaturated.

The emulsion-polymerizable mixture may optionally further include at least one monomeric acrylic or methacrylic acid ester or a polymer thereof, as well as at least one monomeric alkene such as ethylene, or a polymer thereof, or at least one vinylic monomer or polymer, provided that any such additional optional ingredient is addition-polymerizable with the 1,3-diketoamide functional moiety-containing and acid moiety-containing ingredients described above.

Examples of suitable acrylic and methacrylic acid esters include but are not limited to methyl acrylate ("MA"), methyl methacrylate ("MMa"), ethyl acrylate, ethyl methacrylate, propyl acrylate, propyl methacrylate, butyl acrylate ("BA"), butyl methacrylate, 2-ethyl hexyl acrylate ("2-EHA"), 2-ethyl hexyl methacrylate, decyl acrylate, decyl methacrylate, hydroxyethyl acrylate, hydroxyethyl methacrylate ("HEMA"), hydroxypropyl acrylate, hydroxypropyl methacrylate, and combinations thereof.

As was briefly mentioned above, one step of a preferred method of producing the latex formulation of this invention is to combine preselected relative amounts of initiator, surfactant, evaporable aqueous carrier and emulsion-polymerizable ingredients in an agitated reactor of suitable size. Preferably, the reactor is heated to a desired reaction temperature and held at that temperature while the ingredients are added over a predetermined period of time, thereby producing an aqueous polymeric emulsion. Optionally, chain-transfer agent may also be used at this time, if desired.

During the reaction-hold period, while the emulsion-polymerizable ingredients are addition-polymerizing, it may be desirable to incorporate certain additional amounts of initiator or initiators, into the agitated reactor contents, to achieve a desired degree or percentage of conversion or reaction of polymerizable ingredients. Such additional amounts of initiator or ingredients may be the same as or may be different from the initiator ingredient or ingredients selected initially. Again, optional chain-transfer agent may be used, if desired.

For purposes of controlling the viscosity value of the polymeric formulation, it may be necessary to regulate the molecular weight of the polymer being formed. This can be accomplished by the incorporation into the reactor contents of a suitable chain-transfer agent. Suitable chain-transfer agents, to achieve this purpose, are well-known and include various halo-organic compounds such as carbon tetrabromide and dibromodichloromethane; sulfur-containing compounds such as the aklythiols including ethanethiol, butanethiol, tert-butyl and ethyl mercaptoacetate, as well as the aromatic thiols; and various other organic compounds having hydrogen atoms which are readily abstracted by free radicals during polymerization.

The amount of chain-transfer agent needed to achieve a particular molecular weight, moreover, can be estimated by the use of the Mayo equation. (See e.g., pages 226–233 of a text entitled *Principles of Polymerization*, second edition, by George Odian, published 1991 by John Wiley & Sons, Inc.)

Additional suitable chain-transfer agents or ingredients include but are not limited to butyl mercapto propionate; iso octyl mercapto propionic acid; iso octyl mercapto propionate ("IOMP"); bromoform; bromotrichloromethane ("BTCM"); carbon tetrachloride; alkyl mercaptans such as n-dodecyl mercaptan, tertiary-dodecyl mercaptan, octyl mercaptan, tetradecyl mercaptan, and hexadecyl mercaptan; alkyl thioglycolates such as butyl thioglycolate, iso octyl thioglycolate, and dodecyl thioglycolate; thioesters; and combinations thereof.

If the latex formulation contains acid functionality, then upon achieving the described reaction conversion, the pH of the reactor contents will be less than 7, and typically will be in the range of 2.5 to 6. At such pH conditions, the thus-produced addition-polymer particles, which are typically insoluble in the acidic aqueous phase, may give rise to a latex having a milky-white appearance. Regardless of the latex appearance, if the latex formulation contains carboxyl functionality, an effective amount of base is preferably then added to the reactor contents for preventing gellation. Most preferably, the base is a volatile base. The evaporation of the volatile base from the latex formulation enables the final crosslinking reaction of the polymeric ingredients to take place. On the other hand, if the latex formulation of this invention does not contain carboxyl functionality then the use of a base may not be warranted.

If the acid value of the thus-produced emulsion polymer is high (i.e., above about 80 mg of KOH per gram of polymer solids), the thus-produced white-appearing latex of the reaction will dissolve and become a clear solution after addition of the base. This emulsion-polymerization reaction typically results in the production of an alkali-soluble emulsion polymer having
both acid-functional and 1,3-diketoamide functional pendant moieties.

If the acid value of the emulsion polymer is low (below about 80 mg KOH/g of polymer), the polymer will typically not completely dissolve when the basic component is added; and the white, milky appearance may thus persist. The polymer particles may become swollen or may be relatively unaffected by the base, dependent upon the specific monomers used and the acid value of the polymer.

Preferably, the latex formulation, when in the form of a single-package composition, includes an amount of base which is effective for providing extended single-package storage stability, most preferably a volatile base. The amount of base necessary to effectively avoid gellation can be readily determined by a person of ordinary skill without undue experimentation.

As noted previously, a suitable polyfunctional amine-containing compound having at least two amine-functional moieties is also incorporated into the aqueous polymeric emulsion either before storage (a single-package composition) or shortly before use (a two-package composition). Whereas one skilled in the art would expect the polyfunctional amine ingredient of the formulation to crosslink with the 1,3-diketoamide functional groups via enamine formation in a single-package system, and thereby cause gellation, surprisingly, such gellation may be avoided. Without being bound to theory, it is believed that the mechanism for stabilization of the formulation containing both 1,3-diketoamide functional groups and carboxyl functionality is complex and probably results from (a) the base competing with the polyfunctional amine in reaction with the 1,3-diketoamide groups, thereby reducing the degree of crosslinking in the liquid state, and (b) the base neutralizing carboxylic acid groups on the polymer, thereby forming carboxylate ions, which would increase the solubility of the polymer and thereby lead to swelling rather than to agglomeration.

In such single-package formulations, it is believed that at least some of the crosslinking, or in certain situations a major portion of the crosslinking, may be taking place in the liquid phase, possibly within several (i.e., 1 to 4) hours of adding the polyfunctional amine. Accordingly, while not wanting to be tied to conjecture, yet desirous of providing a complete disclosure, it is presently postulated that addition of base to the reactor contents containing both 1,3-diketoamide functional groups and carboxyl functional groups may (1) compete with the amine-functional moieties vis-a-vis the 1,3-diketoamide functional moieties, thereby reducing the degree of crosslinking, and/or (2) enhance the colloidal stability of the polymer dispersion which forms when the crosslinking reaction takes place.

In order to obtain preferred compositions or formulations having superior stability and which provide coatings possessing superior coating properties, it is suggested that the acid value of the polymer be between about 30 and 300, and it is preferred that the acid value of the polymer be between about 50 and 150, which will typically provide an alkali-soluble or alkali-swellable polymer. Since the viscosity of the aqueous composition of matter is very molecular-weight dependent, it is preferred that the molecular weight range of the emulsion polymer be relatively low, in order to maintain desired, low viscosity values at practical solids levels. The Mw of the emulsion polymer should thus be in the range of between about 2,000 and 50,000 and preferably in the range of between about 2,000 to about 40,000, and more preferably in the range of between about 2,000 to about 30,000.

For purposes of dissolving such a polymeric ingredient, i.e., one having both 1,3-diketoamide functional and carboxyl functional moieties, in the aqueous carrier, it has been found that ammonia, an amine, an alkali metal hydroxide, or various combinations of these may be used, if desired. Suitable amines for such a purpose include but are not limited to methyl amine, dimethyl amine, trimethyl amine, ethyl amine, diethyl amine, triethyl amine, propyl amine, dipropyl amine, butyl amine, and combinations thereof. (It is understood that the term "propyl" may include n-propyl, isopropyl and combinations of these, and that the term "butyl" may include n-butyl, sec-butyl, tert-butyl and combinations of these, and so forth.) As noted previously, the most preferred amines are volatile, such as ammonia and other volatile amines.

The latex formulations of this invention may also be prepared using an emulsion polymerization reaction conducted, for example, by performing the step of introducing a major portion of the total amount of initiator, surfactant, optional chain-transfer agent, and evaporable aqueous carrier into the reaction vessel, in the manner described above, and separately performing the step of pre-emulsifying the emulsion-polymerizable mixture in a minor portion of the total amount of initiator, surfactant, optional chain-transfer agent, and evaporable aqueous carrier, for purposes of producing a pre-emulsion mixture; and, thereafter, performing the step of introducing the pre-emulsion mixture into the reaction vessel which already contains the major portion amounts of initiator, surfactant, optional chain-transfer agent, and evaporable aqueous carrier. Preferably, the reaction vessel is heated to the desired reaction temperature prior to adding the pre-emulsion.

In yet another preferred embodiment of the invention, the latex formulation of the present invention includes a mixture of at least two polymeric ingredients. A first polymeric ingredient includes 1,3-diketoamide functional pendant moieties; and a second polymeric ingredient includes acid-functional pendant moieties. Indeed, it is not necessary to have both functionalities in a single polymeric ingredient to achieve satisfactory storage stability of the formulation as well as satisfactory crosslinkability of the resultant polymeric surface coating. In particular, in the case where the formulation contains at least two polymeric ingredients, the formulation can be prepared according to well-known staged polymeric reactions. (See, e.g., U.S. Pat. No. 4,325,856 to Ishikawa et al. or U.S. Pat. No. 4,894,397 to Morgan et al.) In that regard, the 1,3-diketoamide functional moiety-containing polymeric ingredient may be water-insoluble and/or alkali-insoluble; or the 1,3-diketoamide functional moiety-containing polymeric ingredient may be rendered water-soluble and/or alkali-soluble by the incorporation of such monomers as acrylamide and/or acrylamide derivatives, hydroxy-functional monomers, such as hydroxyethyl acrylate, or other monomers known to impart water-solubility to polymers, such as monomers having ethylene oxide chains of predetermined length.

Further in that regard, while the above-described polymeric ingredients of the present invention are preferably made via conventional emulsion-polymerization methods, the above-described polymeric ingredients of the present invention may also be made via conventional solution-polymerization or conventional bulk-polymerization methods, if desired.

For example, suitable conventional methods for producing the alkali-soluble or alkali-swellable polymeric ingredients of the present invention via various well-known solution-polymerization mechanisms are disclosed for example in U.S. Pat. No. 3,673,168 to Burke, Jr., et al.; in U.S. Pat. Nos. 3,753,958 and 3,879,357, both to Wingler et al.; and in U.S. Pat. No. 3,968,059 to Shimada et al. Also, suitable conventional methods for producing the polymeric ingredients of the present invention via conventional bulk-polymerization mechanisms are disclosed in U.S. Pat. No. 4,414,370 to Hamielec et al.; in U.S. Pat. No. 4,529,787 to Schmidt et al.; and in U.S. Pat. No. 4,546,160 to Brand et al.

As was mentioned above, it is believed that the above discussed polymeric ingredients containing the 1,3-diketoamide functional pendent moieties do crosslink to some degree with the amine-functional moieties of the non-polymeric polyfunctional amine when the latter is added to the formulation having carboxyl functionality. It is believed that the lack or delay in onset of gellation may be a result of the presence of the base ingredient in the reactor contents. Thus, in such instances the presence of the base in the single-package latex formulation of this invention is highly preferred. It should be noted however, that if the polymeric ingredient of the latex formulations of this invention does not include carboxyl functionality then the base is not necessary since there is no acid functionality to neutralize even in a single-package system. Significantly, whether a single-package or a two-package latex formulation, all the formulations of the present invention exhibit excellent hydrolytic stability and thus shelf-storage stability, as clearly evidenced by the absence of decomposition products of the 1,3-diketoamide functional pendant moieties during extended storage at elevated temperatures.

In certain situations it may be desirable to utilize the previously discussed latex particles as a support resin in a subsequent polymerization reaction, before any polyfunctional amine is incorporated into the reactor contents. In that regard, the above-described polymerization methods, typically utilized to produce such a latex, are referred to as stage one or the first stage of a 2-stage polymerization procedure and the previously described latex particles are referred to as the stage one polymer.

The subsequent polymerization reaction, referred to as stage two of the 2-stage procedure, is typically utilized for purposes of producing the ultimate film-forming polymeric ingredient or ingredients. Indeed, in the case where the formulation of the invention is an emulsion, and when it is desirable that the discontinuous phase of such an aqueous polymeric emulsion comprise discrete particles of the film-forming polymeric ingredient or ingredients, the latex particles produced via the first-stage polymerization reaction are used as a support resin in the second-stage polymerization procedure, as illustrated by the following description.

Accordingly, into the agitated reactor containing the dissolved or swollen first-stage latex particles is next added a second monomeric mixture specifically formulated as to produce an addition polymer that is insoluble in aqueous media having a pH of 2 to 10. Prior to incorporation of the second monomer mixture into the agitated reactor, however, additional water, surfactant, initiator, and/or optional chain-transfer agent may be added, as desired. The second monomer mixture is fed into the reaction vessel over a predetermined period of time, typically one hour, while the desired second-stage polymerization reaction temperature is maintained, generally between 40° C. to 90° C.

The second-stage monomer mixture generally includes at least one addition-polymerizable monomer, such as acrylic or methacrylic acid ester, a vinyl monomer, a nitrile, or an amide, as described hereinabove. Furthermore, the second-stage monomer mixture may optionally further include an 1,3-diketoamide functional moiety-containing monomer, or an acid moiety-containing monomer, or both, as described above, if desired.

Still further, to produce the second-stage polymer it may be desirable to incorporate an optional crosslinking ingredient or agent into the reactor contents.

In this regard, crosslinking agents that are suitable for purposes of the present invention include but are not limited to divinyl benzene, ethylene glycol diacrylate, ethylene glycol dimethacrylate, trimethylol propane triacrylate, trimethylol propane trimethacrylate, pentaerythritol triacrylate, pentaerythritol trimethacrylate, allyl acrylate, allyl maleate, allyl methacrylate, diallyl maleate, polyethylene glycol diacrylate, and polyethylene glycol dimethacrylate.

Additional crosslinkers, well known to those skilled in the art and suitable for purposes of my present invention, are disclosed in U.S. Pat. No. 3,915,921 to Schlatzer, Jr., in U.S. Pat. No. 4,190,562 to Westeman, and in U.S. Pat No. 4,554,018 to Allen.

During the second-stage reaction-hold period, while the ingredients of the second-stage monomer mixture are addition-polymerizing in the presence of the dissolved or swollen latex particles of the first-stage polymerization, it may be desirable to incorporate further amounts of initiator into the agitated reactor contents to achieve desired conversion of second-stage reaction. Upon achieving desired second-stage reaction conversions, and particularly if the polymeric ingredients include carboxyl functionality, then the pH of the reactor contents may be suitably adjusted, preferably using aqueous ammonia or other base, as previously described, to a pH above 7 and typically in the range of 8 to 9.5. At such pH conditions, the aqueous polymeric emulsion typically consists of insoluble latex particles of second-stage polymer, dispersed throughout the continuous phase of the emulsion.

As was briefly noted above, desired crosslinking, in accordance with one of the several, above-noted features of my present invention, occurs when the 1,3-diketoamide functional moieties desirably react with the amine-functional moieties of the non-polymeric polyfunctional amine. As was also briefly noted above, a preferred water-based latex polymeric formulation of my invention includes carboxyl functionality and in a single-package formulation preferably includes an effective amount of base, particularly volatile base, for inhibiting undesirable reaction between the 1,3-diketoamide functional pendant moieties of the latex particles and the amine-functional moieties of the polyfunctional amine-containing compound, which would otherwise result in gelation. In such a case, the desirable reaction, as between these mutually-reactive moieties, does not fully occur until after evaporation of the volatile components of the novel aqueous polymeric formulation.

Accordingly, when preparing a single-package formulation, a predetermined amount of the above-mentioned polyfunctional amine having at least two amine-functional moieties may, at this point in time, be introduced into the agitated reactor contents, typically over a time period of 5 to 15 minutes or longer. The polyfunctional amine, upon being thus added to the reactor contents, may dissolve in the continuous phase of the emulsion or may become distributed between the continuous and dispersed phases.

In that regard, sufficient polyfunctional amine is thus incorporated into the reactor contents, so as to cause the polymeric composition therein to typically contain about 0.5 to 1.5 1,3-diketoamide functional pendant moieties per amine-functional moiety. Surprisingly, the latex formulation thus produced, i.e., containing 1,3-diketoamide functionality, carboxyl functionality and base in combination with polyfunctional amine, may be stable for at least 12 months when stored at room temperature. If a two-package formulation, then a sufficient amount of polymeric ingredient having 1,3-diketoamide functionality is added to a sufficient amount of a polyfunctional amine to cause the latex formulation to contain about 0.5 to 1.5 1,3-diketoamide functional pendant moieties per amine functional moiety. The pot life of such a two-package formulation of this invention may be from several hours to 5 days depending on the formulation.

The polyfunctional amine-containing compound may be non-polymeric or polymeric, and is preferably non-polymeric. Suitable polymeric amines include, without limitation, polyethylene amine, amine functional polyureas and polyesters, and the like.

The preferred non-polymeric polyfunctional amine-containing compound employed in the latex formulations of this invention possesses at least two amine-functional moieties, typically has a chemical-formula weight of less than about 2,000 grams per mole, and preferably has a chemical-formula weight of less than about 1,000 grams per mole. The non-polymeric polyfunctional amine suitable for purposes of the present invention include aliphatic and cycloaliphatic amines having 2 to 10 primary and/or secondary amino groups and 2 to 100 carbon atoms.

Still further in this regard, suitable non-polymeric polyfunctional amines include but are not limited to hexamethylene, diamine; 2-methyl pentamethylene diamine; 1,3-diamino pentane; dodecane diamine; 1,2-diamino cyclohexane; 1,3-diamino cyclohexane; para-phenylene diamine; 3-methyl piperidine; isophorone diamine; bis-hexamethylene triamine; diethylene triamine; and combinations thereof.

Other non-polymeric polyfunctional amines, which are suitable, include those containing adducts of ethylene and propylene oxide, such as the "JEFFAMINE" series D, ED and T of Texaco Chemical Company of Houston, Tex., U.S.A. preferred non-polymeric polyfunctional amines include 2 to 4 primary amino groups and 2 to 20 carbon atoms. Particularly preferred non-polymeric polyfunctional amines include hexamethylene diamine, diethylene triamine, and combinations thereof.

Until use is desired, the thus-produced crosslinkable, novel aqueous latex formulation can, for example, be stored at room temperature in a convention container such as a metal can, a squeezable plastic tube, a glass bottle, an aerosol container, and so forth When use is desired, if a single-package formulation the crosslinkable aqueous polymeric formulation is applied directly to a suitable substrate or, if a two-package formulation the polymeric ingredient and non-polymeric polyfunctional amine are first mixed and then applied to the substrate. Evaporation of the evaporable components of the aqueous emulsion then occurs over a predetermined period of time, which is typically governed by ambient conditions. Such evaporation enables desirable crosslinking to take place as between the above-discussed mutually-reactive moieties. A crosslinked polymeric surface coating is thus observed to form on the substrate in due course.

The Examples which follow are intended as an illustration of certain preferred embodiments of the invention, and no limitation of the invention is implied.

Example 1

Preparation of 3-isopropenyl-α,α-dimethylbenzylamine

A flask blanketed with nitrogen was charged with 3-isopropenyl-α,α-dimethylbenzylisocyanate (m-TMI) (475.33 g) and the isocyanate was heated to about 85° C. 4-hydroxy-4-methyl-2-pentanone (274.99 g) was added from an addition funnel to the flask at a fairly rapid rate. The mixture was stirred for two hours and about 0.16 g of dibutyltin dilaurate was added to the mixture, after which the temperature was raised to about 100° C. The reaction mixture was stirred for about 1.5 hours at 100° C. and then allowed to cool and stand at room temperature for approximately 48 hours. Subsequently, about 0.14 g of additional dibutyltin laurate was added and heating at 100° C. was resumed. The reaction mixture temperature was then raised to about 125°–130° C. and the mixture was stirred overnight. Water (800 ml) was added to the cooled reaction mixture and the mixture was distilled. The remaining material in the distillation pot was extracted with toluene. The toluene extract was dried with anhydrous $K_2CO_3$, the toluene was distilled and the title product was recovered in a toluene solution.

Example 2

Preparation of 3-isopropenyl-α,α-dimethylbenzyl amidoacetoacetate

A solution of t-butyl acetoacetate (t-BAA) (68.01 g) in toluene (570 ml) was heated to 110° C. and the amine (75.22 g) prepared in Example 1 in toluene (350 ml) was added over a period of about 1–1.25 hours. After all the amine solution was added the reaction mixture was allowed to reflux for 1.5 hours. The toluene and butanol were removed by distillation with the last 10–15% being removed under reduced pressure (30–40 mm). A viscous yellow oil was recovered, which crystallized to form orange-white needles. The structure of the title product was confirmed by infrared spectroscopy, proton and carbon-13 nuclear magnetic resonance spectroscopy.

Example 3

Preparation of an alkali soluble latex polymer having pendant acetoacetamide functional moieties A polymerization reactor was charged with water (539.04 g), ammonium persulfate (2.04 g) and Sipex UB (7.64 g) (an anionic surfactant, sodium lauryl sulfate, available from Rhone-Poulenc, Inc.) A monomer mixture was prepared containing methylmethacrylate (35.91 g), butylacrylate (58.01 g), methacrylic acid (16.57 g), 3-isopropenyl-α,α-dimethylbenzyl amidoacetoacetate (27.62 g) prepared in Example 2 and IOMPA (5.14 g) (iso octyl mercapto propionic acid, a chain transfer agent). The reactor charge was heated to 80° C. and the monomer mixture was fed to the reactor charge for about 1 hour. After all the monomer had been added to the reaction mixture, the mixture was held at 80° C. for about 1 hour. The resulting emulsion was cooled, filtered and contained non-volatiles of about 20.2% by weight.

Comparative Example 1

Preparation of an alkali soluble latex formulation having acetoacetoxy functional pendant moieties A latex formulation was prepared in the same manner as described in Example 3, with the exception that the acetoacetamide functional monomer was replaced by acetoacetoxy ethyl methacrylate (41.43 g) and 29.0 g of methylmethacrylate and 51.1 g of butylacrylate were used to prepare the latex instead of the amounts used in Example 3.

Both latexes of Example 3 and Comparative Example 1 were neutralized with ammonia to a pH of about 7.8–8.0. A 100 g aliquot of each neutralized latex was taken and a stoichiometric amount of 1,6-hexanediamine was added to each. Drawdowns over Lanetta paper and aluminum panels were made and were allowed to stand at room temperature. The films were tested periodically for MEK resistance. The results of these tests are set forth in Table 1.

TABLE 1

| | | MEK RUBS | |
|---|---|---|---|
| Cure Parameters | Substrate | Latex Ex. 1 | Latex Comp. Ex. 1 |
| 2 hours at Room Temp. | Lanetta Charts | 22 | 8 |
| 5 days at Room Temp. | Lanetta Charts | 39 | 28 |
| 5 days at Room Temp. | Aluminum Panels | 60 | 32 |

The results show that the film formed using the novel latex formulation of this invention provided superior solvent resistance to the film formed using a latex formed from acetoacetoxy ethyl methacrylate.

The stability of the latex formulations prepared in Example 3 and Comparative Example 1 were tested by storage at 50° C. over a two-week period. At the end of that time the novel latex formulation of Example 3 was stable, showed no decomposition products and maintained its cure properties. On the other hand, the latex formulation of Comparative Example 1 gelled after one week.

Other variations and modifications of this invention will be obvious to those skilled in this art. This invention is not to be limited except to set forth in the following claims.

What is claimed is:

1. A latex formulation comprising (a) a polymeric ingredient having at least 1,3-diketoamide pendant moieties derived from an ethylenically-unsaturated 1,3-diketoamide functional compound represented by formula (I)

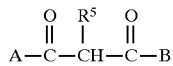

wherein $R^5$ is hydrogen, alkyl having 1 to 10 carbon atoms, aryl having 6 to 20 carbon atoms;

A is a group represented by the formula

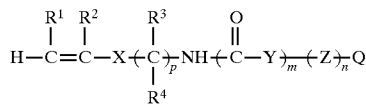

wherein $R^1$ is hydrogen, alkyl having 1 to 10 carbon atoms, aryl having 6 to 20 carbon atoms or aralkyl having 7 to 20 carbon atoms;

$R^2$ is hydrogen, alkyl having 1 to 10 carbon atoms, aryl aryl having 6 to 20 carbon atoms or aralkyl having 7 to 20 carbon atoms;

X arylene having 6 to 20 carbon atoms;

$R^3$ and $R^4$ are independently hydrogen, alkyl having 1 to 10 carbon atoms, aryl having 6 to 20 carbon atoms or aralkyl having 7 to 20 carbon atoms;

Y is —NH— or —O—;

Z is alkylene having 1 to 10 carbon atoms;

m and n are independently 0 or 1;

p is 1;

Q is O or a single bond; and

B is A, an alkyl group having 1 to 10 carbon atoms, aryl having 6 to 20 carbon atoms or aralkyl having 7 to 20 carbon atoms;

(b) a polyfunctional amine; and (c) an evaporable aqueous carrier.

2. A latex formulation according to claim 1, wherein the polyfunctional amine is a non-polymeric polyfunctional amine.

3. A latex formulation according to claim 2, wherein the polymeric ingredient further comprises carboxylic acid functional pendant moieties derived from at least one ethylenically-unsaturated carboxylic acid moiety containing monomer.

4. A latex formulation according to claim 3, further comprising an effective amount of a volatile base to inhibit crosslinking of the polymeric ingredient with the polyfunctional amine while both are present in the aqueous carrier.

5. A latex formulation according to claim 2, wherein x is phenylene.

6. A latex formulation according to claim 5, wherein the ethylencially-unsaturated carboxylic acid moiety containing monomer is selected from the group consisting of methyl acrylate, methyl methacrylate, ethyl acrylate, ethyl methacrylate, propyl acrylate, propyl methacrylate, butyl acrylate, butyl methacrylate, 2-ethyl hexyl acrylate, 2-ethyl hexyl methacrylate, hydroxyethyl acrylate, hydroxyethyl methacrylate, hydroxypropyl acrylate, hydroxypropyl methacrylate and mixtures thereof.

7. A latex formulation according to claim 6, wherein the ethylenically-unsaturated 1,3-diketoamide functional compound is selected from the group consisting of 3-isopropenyl-α,α-dimethylbenzyl amidoacetcacetate, 4-isopropenyl-α,α-dimethylbenzyl amidoacetoacetate, 4-ethylenyl-phenyl amidoacetoacetate and mixtures thereof.

8. A latex formulation comprising:

(a) a polymeric ingredient comprising both acid functional pendant moieties and 1,3-diketoamide functional pendant moieties derived from an ethylenically-unsaturated 1,3-diketoamide functional compound represented by the formula (I)

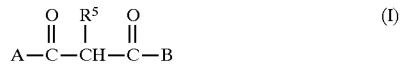

wherein $R^5$ is hydrogen, alkyl having 1 to 10 carbon atoms, aryl having 6 to 20 carbon atoms or aralkyl having 7 to 20 carbon atoms;

A is a group represented by the formula

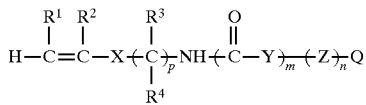

wherein $R^1$ is hydrogen, alkyl having 1 to 10 carbon atoms, aryl having 6 to 20 carbon atoms or aralkyl having 7 to 20 carbon atoms;

$R^2$ is hydrogen, alkyl having 1 to 10 carbon atoms, aryl having 6 to 20 carbon atoms or aralkyl having 7 to 20 carbon atoms;

X arylene having 6 to 20 carbon atoms;

$R^3$ and $R^4$ are independently hydrogen, alkyl having 1 to 10 carbon atoms, aryl having 6 to 20 carbon atoms or aralkyl having 7 to 20 carbon atoms;

Y is —NH— or —O—;

Z is alkylene having 1 to 10 carbon atoms;

m and n and are independently 0 or 1;

p is 1;

Q is O or a single bond; and

B is A, an alkyl group having 1 to 10 carbon atoms, aryl having 6 to 20 carbon atoms or aralkyl having 7 to 20 carbon atoms;

(b) a polyfunctional amine;
(c) an evaporable aqueous carrier; and
(d) an effective amount of base to inhibit crosslinking of the polymeric ingredient with the non-polymeric polyfunctional amine while both are present in the aqueous carrier.

9. A latex formulation according to claim 8, wherein X is phenylene.

10. A latex formulation according to claim 9, wherein the base is ammonia or a volatile amine.

11. A latex formulation according to claim 10, wherein the polyfunctional amine is a non-polymeric polyfunctional amine having a chemical-formula weight of less than about 2000 grams per mole.

12. A latex formulation according to claim 11, wherein the evaporable carrier comprises water and at least one volatile water-miscible liquid organic compound that evaporates at room temperature, and wherein the total amount of volatile organic compound in the formulation does not exceed 200 grams per liter of the formulation.

13. A latex formulation comprising:
(a) A first polymeric ingredient having 1,3-diketoamide function pendant moieties derived from an ethylenically-unsaturated 1,3-diketoamide function compound represented by the formula (I)

wherein $R^5$ is hydrogen, alkyl having 1 to 10 carbon atoms, aryl having 6 to 20 carbon atoms or aralkyl having 7 to 20 carbon atoms;

A is a group represented by the formula

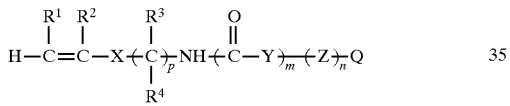

wherein $R^1$ is hydrogen, alkyl having 1 to 10 carbon atoms, aryl having 6 to 20 carbon atoms or aralkyl having 7 to 20 carbon atoms;

$R^2$ is hydrogen alkyl having 1 to 10 carbon atoms, aryl having 6 to 20 carbon atoms or aralkyl having 7 to 20 carbon atoms;

X arylene having 6 to 20 carbon atoms;

$R^3$ and $R^4$ are independently hydrogen, alkyl having 1 to 10 carbon atoms, aryl having 6 to 20 carbon atoms or aralkyl having 7 to 20 carbon atoms;

Y is —NH— or —O—;

Z is alkylene having 1 to 10 carbon atoms m and n are independently 0 or 1;

p is 1;

Q is O or a single bond; and

B is A, an alkyl group having 1 to 10 carbon atoms, aryl having 6 to 20 carbon atoms or aralkyl having 7 to 20 carbon atoms;

(b) a second polymeric ingredient having acid functional pendent moieties;

(c) a polyfunctional amine;

(d) an evaporable aqueous carrier; and (e) an effective amount of base to inhibit crosslinking of the first polymeric ingredient with the non-polymeric polyfunctional amine while both are present in the aqueous carrier.

14. A latex formulation according to claim 13, wherein X is phenylene.

15. A latex formulation according to claim 14, wherein the base is ammonia or a volatile amine.

16. A latex formulation according to claim 15, wherein the polyfunctional amine is a non-polymeric polyfunctional amine having a chemical-formula weight of less than about 2000 grams per mole.

17. A latex formulation according to claim 16, wherein the evaporable carrier comprises water and at least one volatile water-miscible liquid organic compound that evaporates at room temperature, and wherein the total amount of volatile organic compound in the formulation does not exceed 200 grams per liter of the formulation.

* * * * *